(12) United States Patent
Chen et al.

(10) Patent No.: US 11,053,555 B2
(45) Date of Patent: Jul. 6, 2021

(54) METHOD FOR IDENTIFYING GENETIC RELATEDNESS OF LIRIODENDRON HYBRIDS

(71) Applicant: NANJING FORESTRY UNIVERSITY, Nanjing (CN)

(72) Inventors: Jinhui Chen, Nanjing (CN); Jisen Shi, Nanjing (CN); Xiaofei Long, Nanjing (CN); Tielong Cheng, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 0 days.

(21) Appl. No.: 17/042,937

(22) PCT Filed: Oct. 31, 2018

(86) PCT No.: PCT/CN2018/113082
§ 371 (c)(1),
(2) Date: Sep. 29, 2020

(87) PCT Pub. No.: WO2019/223245
PCT Pub. Date: Nov. 28, 2019

(65) Prior Publication Data
US 2021/0032708 A1 Feb. 4, 2021

(30) Foreign Application Priority Data
May 23, 2018 (CN) .......................... 201810498902.0

(51) Int. Cl.
*C12P 19/34* (2006.01)
*C12Q 1/6895* (2018.01)
*C12Q 1/686* (2018.01)

(52) U.S. Cl.
CPC ........... *C12Q 1/6895* (2013.01); *C12Q 1/686* (2013.01); *C12Q 2600/13* (2013.01)

(58) Field of Classification Search
CPC .............................. C12Q 1/6895; C12Q 1/686
See application file for complete search history.

(56) References Cited

FOREIGN PATENT DOCUMENTS

| CN | 101348830 A | 1/2009 |
|---|---|---|
| CN | 108660196 A | 10/2018 |

OTHER PUBLICATIONS

Shaw et al., American Journal of Botany 94(3), 275-288 (2007). (Year: 2007).*
Database accession No. DQ826261 (2007) (Year: 2007).*
Yaqi Zhao, et al., Optimization of a SRAP-PCR System for Analysis of Genetic Diversity of Liriodendron, Scientia Silvae Sinicae, 2014, pp. 37-43, vol. 50 No. 7.
Zhiyong Zhan, et al. Establishment and Optimization of ISSR-PCR System for Liriodendron, Journal of Central South University of Forestry & Technology, 2010, pp. 80-84, vol. 30 No. 6.

* cited by examiner

*Primary Examiner* — Kenneth R Horlick
(74) *Attorney, Agent, or Firm* — Bayramoglu Law Offices LLC

(57) ABSTRACT

A method for identifying the genetic relatedness of *Liriodendron* hybrids is provided, including: 1) extracting DNA of *Liriodendron* hybrid leaves; 2) performing PCR detection; and 3) identifying the genetic relatedness of *Liriodendron* spp. according to the size of PCR products amplified with different primers. A special kit for the method for identifying the genetic relatedness of *Liriodendron* hybrids is further provided, including a primer pair 18.2 and a primer pair 700. Moreover, an application of a special kit for identification of the genetic relatedness of *Liriodendron* hybrids is provided.

7 Claims, 1 Drawing Sheet
Specification includes a Sequence Listing.

US 11,053,555 B2

METHOD FOR IDENTIFYING GENETIC RELATEDNESS OF LIRIODENDRON HYBRIDS

CROSS REFERENCE TO THE RELATED APPLICATIONS

This application is the national phase entry of International Application No. PCT/CN2018/113082, filed on Oct. 31, 2018, which is based upon and claims priority to Chinese Patent Application No. 201810498902.0, filed on May 23, 2018, the entire contents of which are incorporated herein by reference.

TECHNICAL FIELD

The present disclosure belongs to the technical field of tree species identification, and more specifically relates to a method for identifying the genetic relatedness of *Liriodendron* hybrids.

BACKGROUND

*Liriodendron* L. is a plant of the family Magnoliaceae and is one of the ancient genera, including three extant species: *Liriodendron chinense* (Hemsl.) Sarg., *Liriodendron tulipifera* Linn., and their hybrid *Liriodendron chinense×L. tulipifera*. *Liriodendron* serves as an ideal model for studying the historical process of plant evolution, which has great research value.

*Liriodendron chinense* belongs to the national second-class rare and endangered protected plants. It has a straight trunk, can be used as a wood source, and has horseshoe-shaped three-lobed leaves with high ornamental value. *Liriodendron tulipifera* provides excellent wood: light yellow-brown, dense and beautiful in texture, easily processed and used for construction. Moreover, *Liriodendron tulipifera* timber is used for the interior decoration of cabins and trains and for high-grade furniture, and is fast becoming one of the most important tree species for timber usage in the United States. *Liriodendron* hybrids possess the heterosis-related advantages of hybridization with both improved stress resistance and growth characteristics compared to their counterparts of sole Chinese or American origin. However, due to poor natural pollination and the low germination rate of *Liriodendron* plants, current methods for obtaining hybrid species mainly include artificial pollination and graft propagation. These existing methods are relatively complicated. Therefore, there is a need to develop a more convenient and effective method.

The traditional methods for identifying the genetic relatedness of *Liriodendron* hybrids are mostly based on the differences in shape expression (such as morphology and anatomy), isozyme zymograms and other methods. However, morphological markers are greatly affected by the environment and isozyme markers are also affected by gene expression, which limits their use. The emergence of simple sequence repeat (SSR) molecular markers has partly solved some of the difficulties in the identification of genetic relatedness. However, shortcomings remain, such as the low identification accuracy of genetic relatedness, which still cannot meet the requirements.

SUMMARY

Invention objective: to overcome the drawbacks in the prior art, the objective of the present invention is to provide a method for identifying the genetic relatedness of *Liriodendron* hybrids, which can effectively identify the *Liriodendron* hybrids plants at the seedling stage with high speed, high efficiency and accurate results.

Technical solution: to achieve the above-mentioned invention objective, the present invention uses the following technical solution.

A method for identifying genetic relatedness of *Liriodendron* hybrids, including the following steps:

1) extracting DNA from leaves of tree cross offspring;
2) performing polymerase chain reaction (PCR) detection on the extracted DNA;
3) performing PCR amplification with primer pair 18.2, wherein a female parent with a 400 bp specifically-amplified product is identified as *Liriodendron chinense*, and a female parent with a 382 bp specifically-amplified product is identified as *Liriodendron tulipifera*; and
4) performing PCR amplification on the female parent identified as *Liriodendron chinense* with primer pair 700, wherein a female parent with a 700 bp specifically-amplified product is identified as a western provenance *Liriodendron chinense*, and a female parent with a 242 bp specifically-amplified product is identified as an eastern provenance *Liriodendron chinense*; wherein when performing PCR amplification on the female parent identified as *Liriodendron tulipifera* with primer pair 700, a 700 bp specifically-amplified product is obtained.

In step 1), the leaves are newly expanded young leaves and are placed at −80° C. for subsequent use after a liquid nitrogen treatment.

In step 2), the DNA is extracted by a cetyltrimethylammonium bromide (CTAB) method.

In step 3), 10 µL volume for the PCR amplification contains: 75 ng of genomic DNA, 1.0 µL of 10×PCR Buffer, 1.2 µL of 2.5 mM MgCl, 0.2 µL of 10 mM dNTP, 0.5 µL of 10 µM upstream primer of primer pair 18.2, 0.5 µL of 10 µM downstream primer of primer pair 18.2, 0.5 units of Taq enzyme, then adding ddH$_2$O to 10 µL, wherein the sequence of the upstream primer of primer pair 18.2 is AATTCTCT-CAATTTCACTTTGCCT as shown in SEQ ID NO. 1 and the sequence of the downstream primer of primer pair 18.2 is TGGTCGATGCATTCTGTTTCT as shown in SEQ ID NO. 2.

In step 3), a Touch-down PCR amplification program is used, including: pre-denaturation at 95° C. for 4 min, followed by 6 cycles of denaturation at 94° C. for 15 s, renaturation at 60° C. (Δ=−1° C.) for 30 s and extension at 72° C. for 30 s; 24 cycles of denaturation at 94° C. for 15 s, renaturation at 55° C. for 30 s and extension at 72° C. for 30 s, followed by a final extension at 72° C. for 10 min, then storing at 4° C.

In step 4), 10 µL system for the PCR amplification contains: 75 ng of genome DNA, 1.0 µL of 10×PCR Buffer, 1.2 µL of 2.5 mM MgCl, 0.2 µL of 10 mM dNTP, 0.5 µL of 10 µM upstream primer of primer pair 700, 0.5 µL of 10 µM downstream primer of primer pair 700, 0.5 units of Taq enzyme and adding ddH$_2$O to 10 µL, wherein the sequence of the upstream primer of primer pair 700 is TATGGTAT-ATTCTATTCGGTT as shown in SEQ ID NO. 3 and the sequence of the downstream primer of primer pair 700 is TCATTCCAATTCTACCGAT as shown in SEQ ID NO. 4.

In step 4), a Touch-down PCR amplification program is used, including: pre-denaturation at 95° C. for 4 min, followed by 6 cycles of denaturation at 94° C. for 15 s, renaturation at 58° C. (Δ=−1° C.) for 30 s and extension at 72° C. for 45 s; 24 cycles of denaturation at 94° C. for 15 s, renaturation at 55° C. for 30 s and extension at 72° C. for 45 s, followed by a final extension at 72° C. for 10 min, then storing at 4° C.

A special kit for the method of identifying the genetic relatedness of *Liriodendron* hybrids at least includes a primer reagent having a dosage for use equal to or greater than a single use of the primer reagent. The primer sequences of the primer reagent are as follows: the sequence of the upstream primer of primer pair 18.2 is as shown in SEQ ID NO. 1; the sequence of the downstream primer of primer pair 18.2 is as shown in SEQ ID NO. 2; the sequence of the upstream primer of primer pair 700 is as shown in SEQ ID NO. 3; and the sequence of the downstream primer of primer pair 700 is as shown in SEQ ID NO. 4.

The special kit further includes one or more selected from the group consisting of a DNA standard sample reagent, a DNA extraction reagent, and an electrophoresis reagent; and the DNA standard sample reagent includes at least four bands, including a 242 bp band, a 382 bp band, a 400 bp band, and a 700 bp band.

An application of the special kit in the identification of the genetic relatedness of *Liriodendron* hybrids.

Advantages: compared with the prior art, by using the method for identifying the genetic relatedness of *Liriodendron* hybrids and the special kit thereof in the present invention, the genetic relatedness of *Liriodendron* hybrids in a natural forest can be effectively identified at the seedling stage based on the exploration of its chloroplast genome and the characteristics of chloroplast maternal inheritance of *Liriodendron* plants. That is, the unknown *Liriodendron* species can be identified to be a Chinese or American species. Also, the female parent of *Liriodendron* hybrids can be identified to be a Chinese or American species, and thus the male parent type can be inferred. The method and the special kit of the present invention have the advantages of fast speed, high efficiency, accurate results, and good repeatability and stability, showing good practicability.

DETAILED DESCRIPTION OF THE EMBODIMENTS

Figure 1:
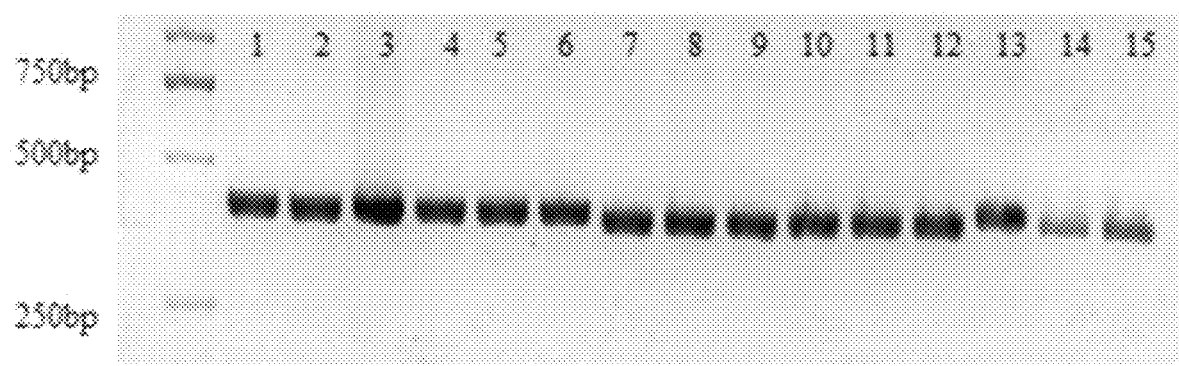
FIG. 1 is a diagram showing electrophoresis results after PCR amplification of various provenances of *Liriodendron* species with primer pair 18.2.

The present invention is further described hereinafter with reference to specific embodiments.

Embodiment 1

A method for identifying the genetic relatedness of *Liriodendron* hybrids is provided, including the following steps:

1) Leaves of *Liriodendron* hybrids are taken at the seedling stage, where the leaves are newly expanded young leaves. After being treated with liquid nitrogen, the leaves are stored at −80° C. for subsequent use. The DNA of the leaves is extracted using a CTAB method; and 2) the extracted DNA is used as a template for performing a first PCR detection and a subsequent second PCR detection.

For the first PCR detection, primer pair 18.2 is used. A female parent with a 400 bp specifically-amplified product is *Liriodendron chinense*. A female parent with a 382 bp specifically-amplified product is *Liriodendron tulipifera*. The specific PCR system and PCR program are as follows:

10 μL system for the PCR amplification contains: 75 ng of genome DNA, 1.0 μL of 10×PCR Buffer, 1.2 μL of 2.5 mM MgCl, 0.2 μL of 10 mM dNTP, 0.5 μL of 10 μM upstream primer of primer pair 18.2, 0.5 μL of 10 μM downstream primer of primer pair 18.2, 0.5 units of Taq enzyme, and adding to 10 μL, wherein the sequence of the upstream primer of primer pair 18.2 is as shown in SEQ ID NO. 1 and the sequence of the downstream primer of primer pair 18.2 is as shown in SEQ ID NO. 2.

The touch-down PCR amplification program includes: pre-denaturation at 95° C. for 4 min, followed by 6 cycles of denaturation at 94° C. for 15 s, renaturation at 60° C. (Δ=−1° C.) for 30 s and extension at 72° C. for 30 s; 24 cycles of denaturation at 94° C. for 15 s, renaturation at 55° C. for 30 s and extension at 72° C. for 30 s, followed by a final extension at 72° C. for 10 min, then storing at 4° C.

For the second PCR detection, PCR amplification is performed on the female parent identified as *Liriodendron chinense* with primer pair 700. A female parent with a 700 bp specifically-amplified product is a *Liriodendron chinense* tree originating from the western provenance. A female parent with a 242 bp specifically-amplified product is a *Liriodendron chinense* tree originating from the eastern provenance. Meanwhile, PCR amplification is performed on the female parent identified as *Liriodendron tulipifera* with primer pair 700, and a 700 bp specifically-amplified product is obtained. The specific PCR system and PCR program are as follows:

10 μL system for the PCR amplification contains: 75 ng of genomic DNA, 1.0 μL of 10×PCR Buffer, 1.2 μL of 2.5 mM MgCl, 0.2 μL of 10 mM dNTP, 0.5 μL of 10 μM upstream primer of primer pair 700, 0.5 μL of 10 μM downstream primer of primer pair 700, 0.5 units of Taq enzyme and adding ddH₂O to 10 μL, wherein the sequence of the upstream primer of primer pair 700 is as shown in SEQ ID NO. 3 and the sequence of the downstream primer of primer pair 700 is as shown in SEQ ID NO. 4.

The touch-down PCR amplification program includes: pre-denaturation at 95° C. for 4 min, followed by 6 cycles of denaturation at 94° C. for 15 s, renaturation at 58° C. (Δ=−1° C.) for 30 s, and extension at 72° C. for 45 s; 24 cycles of denaturation at 94° C. for 15 s, renaturation at 55° C. for 30 s and extension at 72° C. for 45 s, followed by a final extension at 72° C. for 10 min, then storing at 4° C.

As shown in FIG. 1, PCR amplification is performed on various provenances of *Liriodendron* species with primer pair 18.2, and the amplification results are interpreted by 3% agarose gel electrophoresis. In FIG. 1, lanes 1-3 are three random samples originating from a provenance near Lushan City in Jiangxi Province; lanes 4-6 are three random samples originating from a provenance near Monan City in Guizhou Province; lanes 7-9 are three random samples originating from a provenance near South Carolina in North America; lanes 10-12 are three random samples originating from a provenance near Ontario in North America; and lanes 13-15 are samples from a provenance near Lushan City, S.C. (North America), and Fi offspring obtained by cross-breeding a tree originating from the South Carolina provenance as the female parent with a tree from the Lushan provenance as the male parent, respectively. The sizes of the PCR products in lanes 1-6 are all 400 bp. The sizes of the PCR products in lanes 7-12 are all 382 bp. The size of the PCR product in lane 13 is 400 bp. The size of the PCR product in lane 14 is 382 bp. The size of the PCR product in lane 15 is 382 bp. It can be seen that, with primer pair 18.2, a 400 bp specifically-amplified product can be obtained by PCR amplification on *Liriodendron chinense* and a 382 bp specifically-amplified product can be obtained by PCR amplification on *Liriodendron tulipifera*. A band of the specifically-amplified product obtained by performing PCR amplification on the hybrid offspring has the same size as that of the specifically-amplified product obtained by performing PCR amplification on the female parent.

Figure 2:
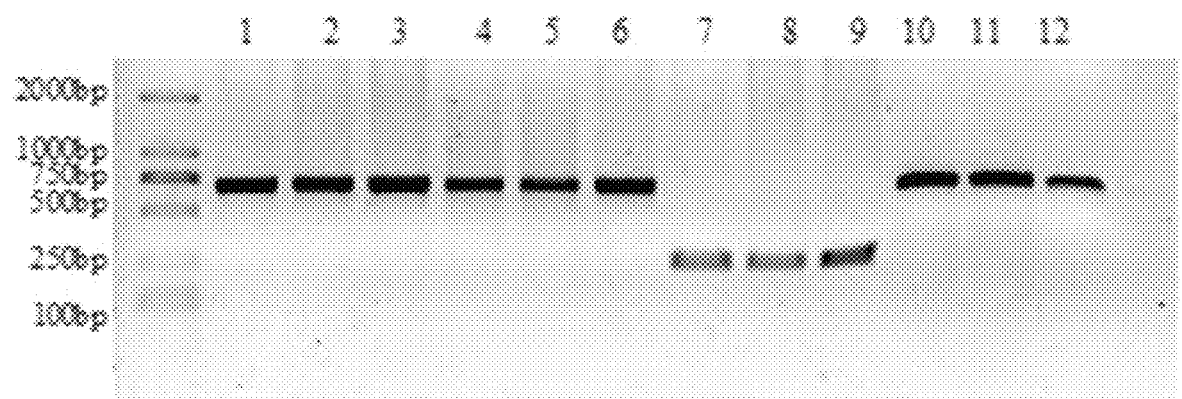
FIG. 2 is a diagram showing electrophoresis results after PCR amplification of various provenances of *Liriodendron* species with primer pair 700.

As shown in FIG. 2, PCR amplification is performed on *Liriodendron* species originating from various provenances with primer pair 700 and the amplification results are interpreted by 3% agarose gel electrophoresis. In FIG. 2, lanes 1-3 are three random samples originating from a provenance near Monan City in Guizhou Province; lanes 4-6 are three random samples originating from a provenance near South Carolina in North America; lanes 7-9 originating from a provenance near Lushan City in Jiangxi Province; and lanes 10-12 are three random samples originating from a provenance near Ontario in North America. The sizes of the PCR products in lanes 1-6 are all 700 bp. The sizes of the PCR products in lanes 7-9 are all 242 bp. The sizes of the PCR products in lanes 10-12 are all 700 bp. It can be seen that, with primer pair 700, a 700 bp specifically-amplified product can be obtained by PCR amplification on *Liriodendron chinense* from western provenances, a 242 bp specifically-amplified product can be obtained by PCR amplification on *Liriodendron chinense* from eastern provenances and a 700 bp specifically-amplified product can be obtained by PCR amplification on *Liriodendron tulipifera*.

In this embodiment, the genetic relatedness of *Liriodendron* hybrids can be identified by combining two primers pairs. Primer pair 18.2 can be used to preliminarily identify whether the female parent of *Liriodendron* hybrids is *Liriodendron chinense* or *Liriodendron tulipifera*; then primer pair 700 can be used to further identify whether the female parent of *Liriodendron* hybrids, whose female parent has been identified as *Liriodendron chinense*, originates from the eastern or western provenance.

Embodiment 2

A special kit for the method of Embodiment 1 is provided, including a primer reagent having sufficient dosage for usage equal to or greater than a single use of the primer reagent. The primer reagent has two primer pairs in total, and the dosage is sufficient for more than 25 reactions. The specific primer sequences are as follows: The sequence of the upstream primer of the primer pair 18.2 is as shown in SEQ ID NO. 1.

The sequence of the downstream primer of the primer pair 18.2 is as shown in SEQ ID NO. 2.

The sequence of the upstream primer of the primer pair 700 is as shown in SEQ ID NO. 3.

The sequence of the downstream primer of the primer pair 700 is as shown in SEQ ID NO. 4.

Preferably, the special kit includes a DNA standard sample reagent having sufficient dosage for more than 25 reactions, a DNA extraction reagent having sufficient dosage for more than 25 reactions, a PCR reagent having sufficient dosage for more than 25 reactions, and an electrophoresis reagent having sufficient dosage for more than 25 reactions.

The DNA standard sample contains at least four bands, including a 242 bp band, a 382 bp, band, a 400 bp band, and a 700 bp band.

The DNA extraction reagent is a necessary reagent used for the CTAB method.

The PCR reagent is a general reagent for the PCR amplification system.

The electrophoretic reagent is a general electrophoretic reagent.

The special kit is used to identify the genetic relatedness of *Liriodendron* hybrids. The method is the same as that in Embodiment 1, and the identification results are similar to those in Embodiment 1. The special kit is convenient and efficient in use.

What is claimed is:

1. A method for identifying genetic relatedness of *Liriodendron* hybrids, comprising the following steps:
   1) extracting DNA from leaves of tree cross offspring to obtain an extracted DNA;
   2) performing a first PCR detection and then a second PCR detection on the extracted DNA, wherein in the first PCR detection, performing a first PCR amplification with primer pair 18.2 on the extracted DNA, and then
   identifying a female parent with a 400 bp specifically-amplified product as *Liriodendron chinense*, and identifying a female parent with a 382 bp specifically-amplified product as *Liriodendron tulipifera*; and
   wherein in the second PCR detection, performing a second PCR amplification on the female parent identified as *Liriodendron chinense* with primer pair 700, performing a third PCR amplification on the female parent identified as *Liriodendron tulipifera* with the primer pair 700 to obtain a 700 bp specifically-amplified product, identifying a female parent with the 700 bp specifically-amplified product as a *Liriodendron chinense* tree originating from a western provenance, and identifying a female parent with a 242 bp specifically-amplified product as a *Liriodendron chinense* tree originating from an eastern provenance;
   wherein, a sequence of a first upstream primer of the primer pair 18.2 is shown in SEQ ID NO. 1, and a sequence of a first downstream primer of the primer pair 18.2 is shown in SEQ ID NO. 2; a sequence of a second upstream primer of the primer pair 700 is shown in SEQ ID NO. 3, and a sequence of a second downstream primer of the primer pair 700 is shown in SEQ ID NO. 4;
   wherein, the western provenance is a Monan provenance of Guizhou province, and the eastern provenance is a Lushan provenance of Jiangxi province.

2. The method for identifying the genetic relatedness of the *Liriodendron* hybrids according to claim 1, wherein, in step 1), the leaves are newly expanded young leaves and are placed at −80° C. for subsequent use after a liquid nitrogen treatment.

3. The method for identifying the genetic relatedness of the *Liriodendron* hybrids according to claim 1, wherein, in step 1), the DNA is extracted by a cetyltrimethylammonium bromide (CTAB) method.

4. The method for identifying the genetic relatedness of the *Liriodendron* hybrids according to claim 1, wherein, in the first PCR detection, a 10 μL system for the first PCR amplification comprises: 75 ng of genomic DNA, 1.0 μL of 10×PCR Buffer, 1.2 μL of 2.5 mM MgCl, 0.2 μL of 10 mM dNTP, 0.5 μL of 10 μM of the first upstream primer of the primer pair 18.2, 0.5 μL of 10 μM of the first downstream primer of the primer pair 18.2, 0.5 units of Taq enzyme and adding ddH$_2$O to 10 μL; wherein, the sequence of the first upstream primer of the primer pair 18.2 is shown in SEQ ID NO: 1 and the sequence of the first downstream primer of the primer pair 18.2 is shown in SEQ ID NO: 2.

5. The method for identifying the genetic relatedness of the *Liriodendron* hybrids according to claim 1, wherein, in the first PCR detection, a Touch-down PCR amplification program is used, comprising: pre-denaturation at 95° C. for 4 min, followed by 6 cycles of denaturation at 94° C. for 15 s, renaturation at 60° C.Δ=−1° C. for 30 s, and extension at 72° C. for 30 s; 24 cycles of denaturation at 94° C. for 15 s, renaturation at 55° C. for 30 s, and extension at 72° C. for 30 s, followed by a final extension at 72° C. for 10 min, then storing at 4° C.

6. The method for identifying the genetic relatedness of the *Liriodendron* hybrids according to claim 1, wherein, in the second PCR detection, a 10 μL system for the second PCR amplification and the third PCR amplification comprises: 75 ng of genomic DNA, 1.0 μL of 10×PCR Buffer, 1.2 μL of 2.5 mM MgCl$_2$, 0.2 μL of 10 mM dNTP, 0.5 μL of 10 μM of the second upstream primer of the primer pair 700, 0.5 μL of 10 μM of the second downstream primer of the primer pair 700, 0.5 units of Taq enzyme, and adding ddH$_2$O to 10 μL, wherein, the sequence of the second upstream primer of the primer pair 700 is shown in SEQ ID NO: 3 and the sequence of the second downstream primer of the primer pair 700 is shown in SEQ ID NO: 4.

7. The method for identifying the genetic relatedness of the *Liriodendron* hybrids according to claim 1, wherein, in the second PCR detection, a Touch-down PCR amplification program is used, comprising: pre-denaturation at 95° C. for 4 min, followed by 6 cycles of denaturation at 94° C. for 15 s, renaturation at 58° C.Δ=−1° C. for 30 s, and extension at 72° C. for 45 s; 24 cycles of denaturation at 94° C. for 15 s, renaturation at 55° C. for 30 s, and extension at 72° C. for 45 s, followed by a final extension at 72° C. for 10 min, then storing at 4° C.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 1
aattctctca atttcactttt gcct                24

<210> SEQ ID NO 2
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 2
tggtcgatgc attctgtttc t                21

<210> SEQ ID NO 3
<211> LENGTH: 21
<212> TYPE: DNA
<213> ORGANISM: Artificial Sequence -continued

```
<220> FEATURE:
<223> OTHER INFORMATION: The sequence is synthetized.

<400> SEQUENCE: 3
tatggtatat tctattcggt t                                          21

<210> SEQ ID NO 4
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 4
tcattccaat tctaccgat                                             19
```